United States Patent [19]
Wolf et al.

[11] Patent Number: 5,928,245
[45] Date of Patent: *Jul. 27, 1999

[54] DEFORMABLE INTRAOCULAR LENS INJECTING APPARATUS WITH TRANSVERSE HINGED LENS CARTRIDGE

[75] Inventors: John R. Wolf, San Moreno; Vladimir Feingold, Laguna Niguel; Thomas J. Chambers, Upland; Daniel C. Eagles, Capistrano Beach, all of Calif.

[73] Assignee: Staar Surgical Company, Inc., Monrovia, Calif.

[*] Notice: This patent is subject to a terminal disclaimer.

[21] Appl. No.: 08/691,491

[22] Filed: Aug. 2, 1996

Related U.S. Application Data

[63] Continuation-in-part of application No. 08/649,433, May 17, 1996, application No. 08/570,564, Dec. 11, 1995, application No. 08/547,908, Oct. 25, 1995, application No. 08/547,295, Oct. 25, 1995, application No. 08/449,103, May 24, 1995, application No. 08/403,530, Mar. 14, 1995, application No. 08/401,523, Mar. 10, 1995, application No. 08/368,792, Jan. 4, 1995, application No. 08/345,360, Nov. 18, 1994, application No. 08/240,520, Jul. 19, 1994, application No. 08/220,999, Apr. 1, 1994, abandoned, application No. 08/196,855, Feb. 15, 1994, application No. 08/195,717, Feb. 14, 1994, and application No. 07/953,251, Sep. 30, 1992, abandoned.

[51] Int. Cl.[6] .......................................... A61F 9/00
[52] U.S. Cl. ................................. 606/107; 623/6
[58] Field of Search ............................... 606/107; 623/4, 623/6

[56] References Cited

U.S. PATENT DOCUMENTS

| 4,836,201 | 6/1989 | Patton et al. . | |
| 5,304,182 | 4/1994 | Rheinish et al. | 606/107 |
| 5,468,246 | 11/1995 | Blake | 606/107 |
| 5,474,562 | 12/1995 | Orchowski et al. | 606/107 |
| 5,578,042 | 11/1996 | Cumming | 606/107 |
| 5,616,148 | 4/1997 | Eagles et al. | 606/107 |

*Primary Examiner*—Glenn K. Dawson
*Attorney, Agent, or Firm*—Klima & Pezzlo PC

[57] ABSTRACT

A deformable intraocular lens injecting apparatus including a transverse hinged lens cartridge for allowing the lens cartridge to be opened and closed for loading the deformable intraocular lens into the lens cartridge. A preferred embodiment includes a lens cartridge including a lens holding portion connected to a nozzle portion. In this preferred embodiment, the lens holding portion includes a movable wall portion with a protrusion for folding the deformable intraocular lens into a lens delivery passageway of the lens cartridge when closing the movable wall portion.

33 Claims, 5 Drawing Sheets

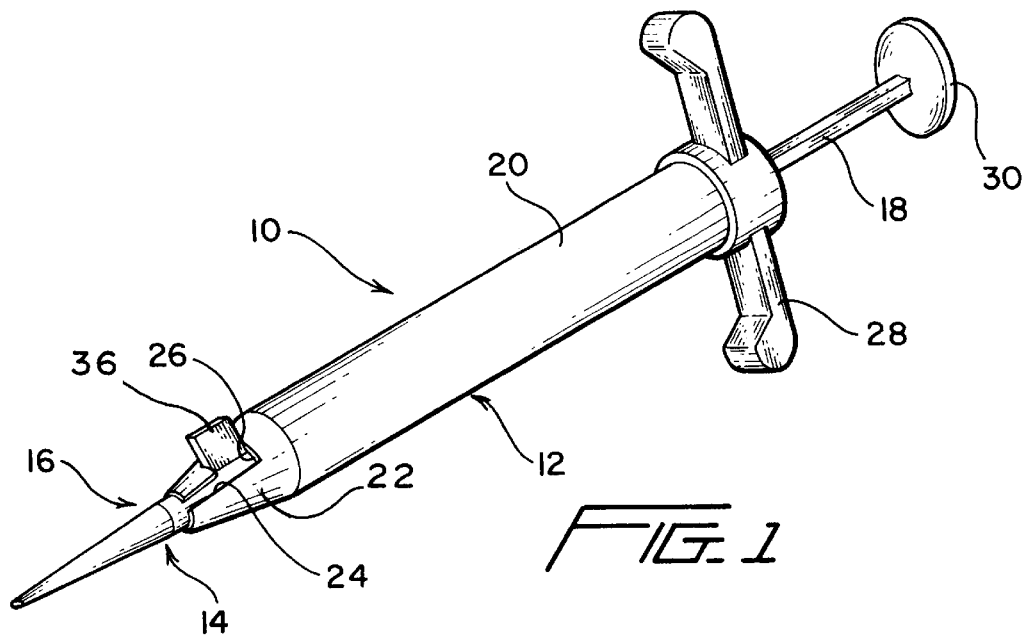
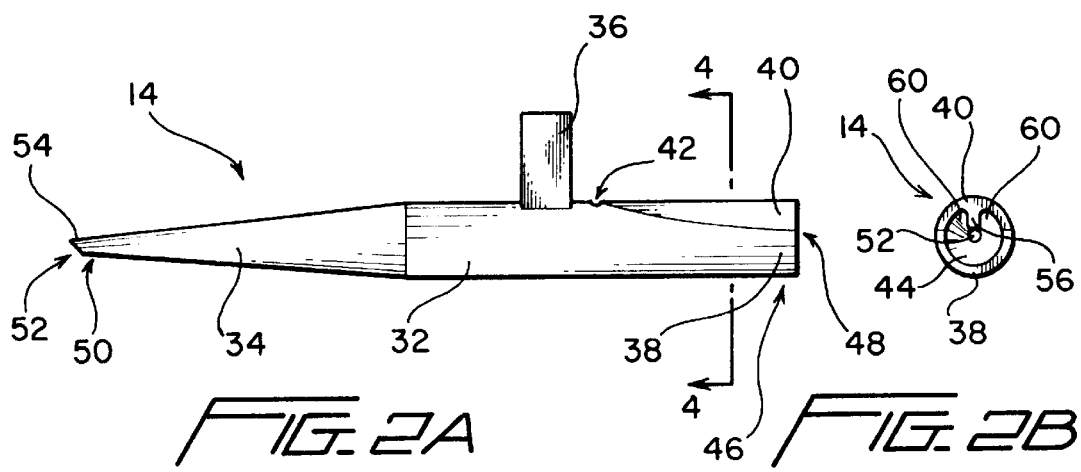
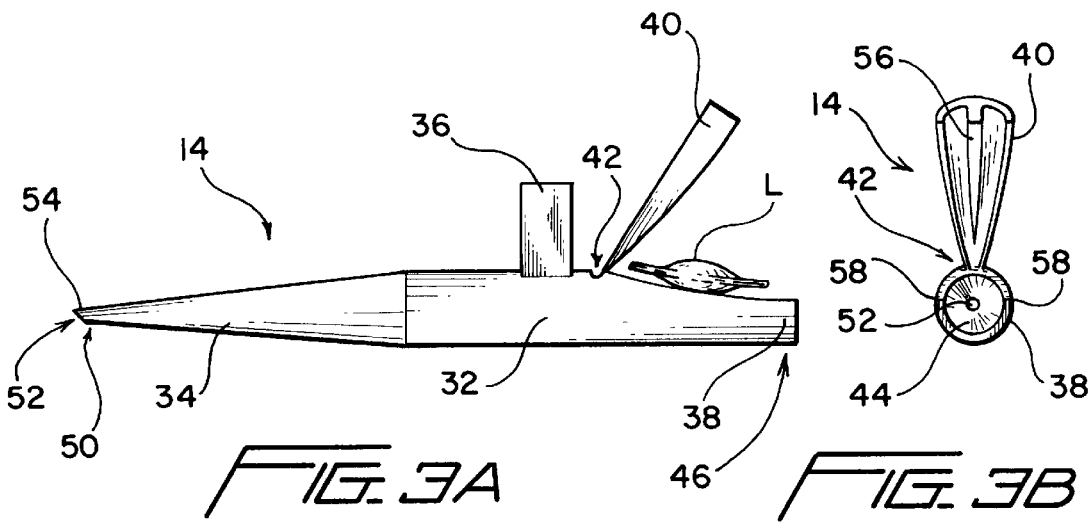

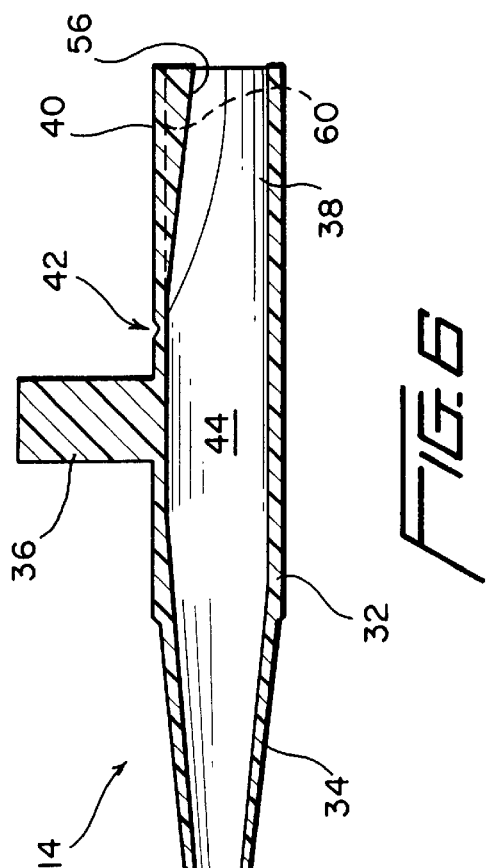
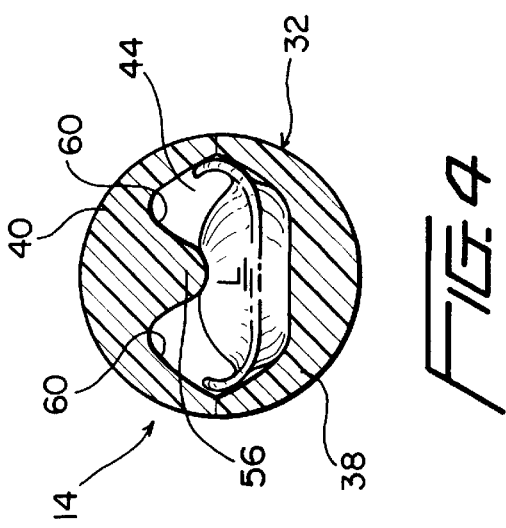
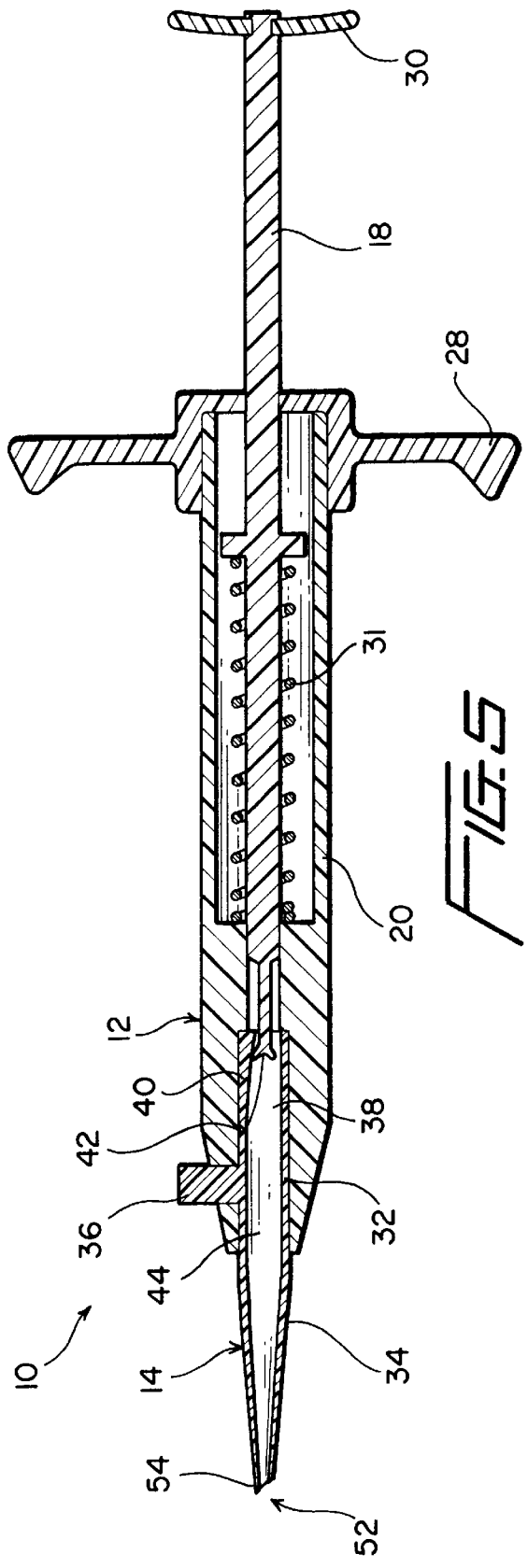

DEFORMABLE INTRAOCULAR LENS INJECTING APPARATUS WITH TRANSVERSE HINGED LENS CARTRIDGE

RELATED APPLICATIONS

This is a Continuation-In-Part (CIP) of:
1) U.S. Patent Application entitled "Apparatus and Method for Preparing an Intraocular Lens for Insertion", Ser. No. 08/649,433, filed May 17, 1996;
2) U.S. Patent Application entitled "Deformable Intraocular Lens Injecting Apparatus with Deformable Tip Plunger", Ser. No. 08/570,564, filed Dec. 11, 1995;
3) U.S. Patent Application entitled "Transverse Hinged Deformable Intraocular Lens Injecting Apparatus", Ser. No. 08/547,908, filed Oct. 25, 1995;
4) U.S. Patent Application entitled "Transverse Hinged Deformable Intraocular Lens Injecting Apparatus", Ser. No. 08/547,295, filed Oct. 25, 1995;
5) U.S. Patent Application entitled "Deformable Intraocular Lens Injection System, and Method Thereof", Ser. No. 08/449,103, filed May 24, 1995;
6) U.S. Patent Application entitled "Deformable Intraocular Lens Injecting Device, Ser. No. 08/403,530, filed Mar. 14, 1995;
7) U.S. Patent Application entitled "Deformable Intraocular Lens Insertion System", Ser. No. 401,523, filed Mar. 10, 1995;
8) U.S. Patent Application entitled "Deformable Intraocular Lens Injection Systems and Methods of Use Thereof", Ser. No. 08/368,792, filed Jan. 4, 1995;
9) U.S. Patent Application entitled "Disposable Intraocular Lens Insertion System, Ser. No. 08/345,360, filed Nov. 18, 1994;
10) U.S. Patent Application entitled "Intraocular Lens Insertion System", Ser. No. 08/240,520, filed Jul. 19, 1994;
12) U.S. Patent Application entitled "Method for the Surgical Implantation of a Deformable Intraocular Lens in the Eye", Ser. No. 08/220,999, filed Apr. 1, 1994, now abandoned;
14) U.S. Patent Application entitled "Hingeless Cartridge for Insertion of a Deformable Intraocular Lens", Ser. No. 08/196,855, filed Feb. 15, 1994;
15) U.S. Patent Application entitled "Methods for Implantation of a Deformable Intraocular Lens, Ser. No. 08/195,717, filed Feb. 14, 1994; and
16) U.S. Patent Application entitled "Intraocular Lens Insertion System", Ser. No. 07/953,251, filed Sep. 30, 1992, now abandoned,
all fully incorporated herein by reference.

FIELD OF THE INVENTION

This invention is directed to a deformable intraocular lens injecting apparatus including a transverse hinged closure for loading the deformable intraocular lens into a lens delivery passageway of the lens injecting apparatus. In a preferred embodiment, the lens injecting apparatus includes a lens cartridge having a transverse hinged configured to open and close for loading the deformable intraocular lens into a lens delivery passageway of the lens cartridge.

BACKGROUND OF THE INVENTION

The present invention is directed to surgical apparatus for the implantation of a deformable intraocular lens into the eye. STAAR Surgical Company of Monrovia, Calif. developed the concept of using a "shooter" type device for implanting a deformable intraocular lens into the eye, and supplied such devices in the United States beginning around 1986.

The STAAR "shooter" apparatus includes a separate lens injecting device and a separate one-piece hinged cartridge (i.e. a lens holding portion connected to a nozzle portion) that can be assembled together for operation. The hinged cartridge opens along a longitudinal axis to allow a deformable intraocular lens to be loaded in a flat configuration in the two open halves of the lens delivery passageway. When the lens cartridge is closed, a lens delivery passageway is defined therein and the deformable intraocular lens is folded about its center into a curved folded configuration inside the lens delivery passageway. The loaded lens cartridge is then assembled with the lens injecting device which includes a lens is cartridge receiver and a movable plunger for forcing the deformable intraocular lens along the lens delivery passageway into the eye.

SUMMARY OF THE INVENTION

An object of the present invention is to provide an improved deformable intraocular lens injecting apparatus.

A second object of the present invention is to provide an improved deformable intraocular lens injecting apparatus including an improved lens cartridge.

A third object of the present invention is to provide a lens cartridge which is easy to load with a deformable intraocular lens.

A fourth object of the present invention is to provide a deformable intraocular lens injecting apparatus including a transverse hinged lens cartridge configured to open and close for loading the deformable intraocular lens into the lens cartridge.

A fifth object of the present invention is to provide a deformable intraocular lens injecting apparatus including a hinged lens cartridge and a lens injecting device including a lens cartridge receiver and a movable plunger.

A sixth object of the present invention is to provide a deformable intraocular injecting apparatus including a lens cartridge having a lens holding portion connected to a nozzle portion, the lens holding portion including wall portions connected together by a transverse hinge and configured to be opened and closed for loading a deformable intraocular lens into the lens cartridge.

A seventh object of the present invention is to provide a deformable intraocular lens injecting apparatus including a lens cartridge having a lens holding portion connected to a nozzle portion, the lens holding portion including a movable wall portion connected to a stationary wall portion by a transverse hinge.

A eighth object of the present invention is to provide a deformable intraocular lens injecting apparatus including a lens cartridge having a lens holding portion connected to a nozzle portion, the lens holding portion including a movable wall portion connected to a stationary wall portion by a transverse hinge, and the movable wall portion including a protrusion extending inwardly into the lens delivery passageway for folding the deformable intraocular lens into the lens delivery passageway when closing the movable wall portion.

The present invention is directed to a lens injecting apparatus for implanting a deformable intraocular lens into the eye. The lens injecting apparatus is provided with a lens delivery passageway therethrough accessible by means of a transverse hinged closure.

In one preferred embodiment, the lens injecting apparatus is a one (1) piece or component arrangement (i.e. no lens cartridge). For example, the lens injecting apparatus comprises a housing with an injecting tip and a passageway provided therethrough, a movable plunger disposed within said housing, and a transverse hinged closure along the side of the housing to allow a deformable intraocular lens to be loaded through an opening or window through the side of the housing into the lens delivery passageway when the transverse hinged closure is opened, and seal the opening or window when the transverse hinged closure is closed.

In another preferred embodiment, the lens injecting apparatus is a two (2) piece or component arrangement, including 1) a lens injecting device including a lens cartridge receiver; and 2) a lens cartridge. For example, the lens injecting device comprises a housing, a lens cartridge receiver provided at one end of the housing, and a movable plunger disposed in the housing. The lens cartridge, for example, is a one (1) piece or component arrangement including a lens holding portion having a transverse hinged closure connected to a nozzle portion. Once a deformable intraocular lens is loaded into the lens cartridge, the lens cartridge is then loaded into the lens cartridge receiver of the lens injecting device.

The transverse hinged closure arrangement utilized in the lens injecting apparatus according to the present invention orients the hinge transverse relative to the orientation of the lens delivery passageway. Specifically, the axis of the hinge is not parallel with the longitudinal axis of the lens delivery passageway. Preferably, the axis of the hinge is set at forty-five (45) to ninety (90) degrees relative to the longitudinal axis of the lens delivery passageway. An angle of ninety (90) degrees is most preferred, especially in embodiments where the transverse hinged closure is utilized for folding the deformable intraocular lens into the lens delivery passageway so that the portion of the transverse hinged closure contacting and forcing the deformable intraocular lens into the lens delivery passageway is aligned with the lens delivery passageway.

In a preferred embodiment, the lens delivery passageway is linear, however, curvilinear arrangements can be utilized. Further, the lens delivery passageway may be contoured (e.g. include one or more grooves) for further folding the deformable intraocular lens as it is moved along or through the lens delivery passageway. In addition, the lens delivery passageway may taper inwardly in a direction of advancement of the deformable intraocular lens through the lens delivery passageway.

Preferably, the transverse hinged closure is configured to substantially seal the lens delivery passageway when closed to prevent the deformable intraocular lens from escaping when the deformable intraocular lens is being forced through the lens delivery passageway. In some embodiments, the transverse hinged closure provides little or none compressive force on the deformable intraocular lens loaded into the lens delivery passageway when the transverse hinged closure is fully closed. In other embodiments, the transverse hinged closure purposely provides compressive forces on the deformable intraocular lens loaded into the lens delivery passageway when the transverse hinged closure is fully closed.

In other embodiments, the transverse hinged closure does not seal the lens delivery passageway, but instead is used to fold the lens into the lens delivery passageway when the transverse hinged closure is being closed. If the deformable intraocular lens is sufficiently folded and captured inside the lens delivery passageway, the deformable intraocular lens can be advanced past the location of the transverse hinged closure, for example by the plunger tip, to a forward portion of the lens injecting apparatus. The forward portion of the lens injecting apparatus can have a completely closed lens delivery passageway portion having an inwardly tapering or lens folding configuration providing radially inwardly directed compressive forces to be exerted onto the deformable intraocular lens by the inner walls of the lens delivery passageway as the deformable intraocular lens is being advanced therethrough.

The transverse hinged closure is preferably arranged to stay closed when shut, and more preferably positively locks when shut (e.g. releasably locks to allow reopening for inspection of lens or reuse of lens injecting apparatus, or permanently locks preventing reopening and reuse). In some preferred embodiments, the inner surface of the transverse hinged closure serves as an inner wall of the lens delivery passageway, preferably contiguous with remaining inner wall portions of the lens injecting apparatus. Further, the inner surface of the transverse hinged closure can be contoured (e.g. provided with at least one groove, protrusion, or complex contoured surface design) to facilitate folding of the deformable intraocular lens when closing the transverse hinged closure and/or when advancing the deformable intraocular lens through the lens delivery passageway.

In the preferred two (2) piece or component arrangement, the transverse hinged lens cartridge is held closed once inserted into the lens receiver of the lens injecting device. For example, a cylindrical portion of the housing of the lens injecting device serves as a lens cartridge receiver, and the band strength of the cylindrical portion maintains the transverse hinged lens cartridge closed when the lens cartridge is inserted into the lens cartridge receiver.

In one preferred embodiment, the transverse hinged closure includes a protrusion for forcing the center of the deformable intraocular lens downwardly while the ends of the lens are held by sides of an opening through the side of the housing to cause the deformable intraocular lens to fold into the lens delivery passageway as the transverse hinged closure is being closed.

In another preferred embodiment, the deformable intraocular lens injecting apparatus includes a lens injecting device and a lens cartridge receiver. The lens cartridge of the present invention has a lens holding portion connected to a nozzle portion. Together, the lens holding portion and the nozzle portion define a lens delivery passageway, through which a deformable intraocular lens is introduced to the capsule of the eye. The longitudinal axis of the lens cartridge is substantially parallel to the lens delivery passageway.

The lens holding portion of the lens cartridge of the present invention includes a movable wall portion which is movably connected to a stationary wall portion. The movable wall portion moves about an axis which is not parallel to the longitudinal axis of the lens cartridge. In the most preferred embodiment of the present invention, the movable wall portion swings about a transverse hinge which connects the movable wall portion to the stationary wall portion. The transverse hinge is configured in the most preferred embodiment so that there exists a plane normal to the axis of the transverse hinge which contains the longitudinal axis of the lens cartridge.

The lens cartridge of the present invention also includes means for releasably locking the lens cartridge in the lens injecting device. In the most preferred embodiment of the present invention, an extension is included on the lens holding portion of the lens cartridge. The extension engages an L-shaped slot in the lens injecting device to releasably lock the lens cartridge therein.

In use, the stationary wall portion of the lens cartridge is grasped in a first hand of the user. With a second hand, the user opens the lens cartridge by pushing the movable wall portion about the transverse hinge to expose a substantial portion of the lens delivery passageway of the lens cartridge. While the lens cartridge is in an open configuration, a deformable intraocular lens is placed on the exposed lens delivery passageway. The user then closes the movable wall portion to complete the loading of the lens in the lens cartridge. The lens cartridge is then ready for assembly with the lens injecting device. Grasping the lens cartridge in the first hand and the lens injecting device in the second hand, the extension of the lens cartridge is aligned with the L-shaped slot in the lens injecting device. The lens cartridge is then guided into slot in the lens injecting device to releasably lock the lens cartridge therein.

Thus, the user of the lens injecting apparatus of the present invention may more easily load a deformable intraocular lens into the lens cartridge. Further, the user may more easily assemble the lens cartridge with the lens injecting device. In short, the deformable intraocular lens implantation procedure is improved.

BRIEF DESCRIPTION OF THE DRAWINGS

FIG. 1 is a perspective view of a deformable intraocular lens injecting apparatus according to the present invention.

FIG. 2A is a side elevational view of a first preferred embodiment of a lens cartridge according to the present invention in a closed configuration.

FIG. 2B is a cross-sectional view of at the lens cartridge shown in FIG. 2A.

FIG. 3A is a side elevational view of the lens cartridge shown in FIG. 2A in an open configuration.

FIG. 3B is a rear end elevational view of the lens cartridge shown in FIG. 3A.

FIG. 4 is a cross-sectional view of the lens cartridge as indicated in FIG. 2A loaded with a partially folded deformable intraocular lens.

FIG. 5 is a longitudinal cross-sectional view of the lens injecting apparatus shown in FIG. 1.

FIG. 6 is a longitudinal cross-sectional view of the lens cartridge shown in FIGS. 2A and 2B.

DETAILED DESCRIPTION OF PREFERRED EMBODIMENTS

Figure 7:
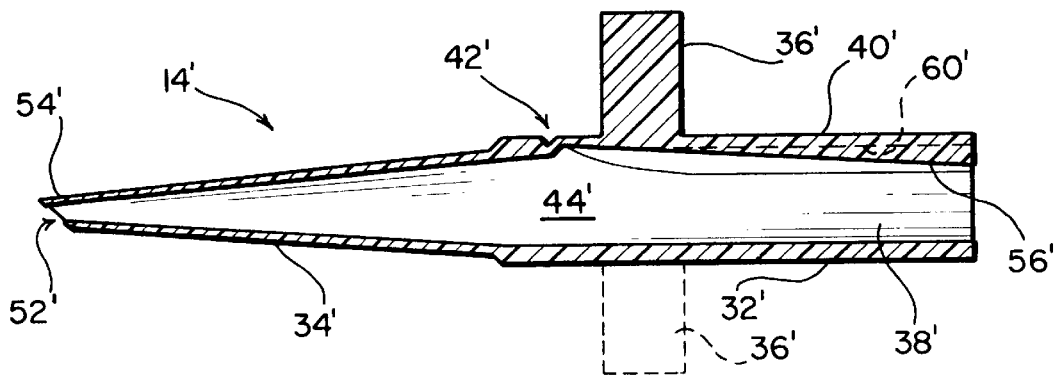
FIG. 7 is a longitudinal cross-sectional view of a second preferred embodiment of the lens cartridge according to the present invention.

A preferred deformable intraocular lens injecting apparatus 10 according to the present invention is shown in FIGS. 1 to 6.

The lens injecting apparatus 10 comprises two (2) separate main components including 1) a lens injecting device 12; and 2) a lens cartridge 14. The lens injecting apparatus 10 is shown fully assembled in FIG. 1 with the lens cartridge 14 connected to the lens injecting device 12.

The lens injecting device 12 comprises a lens cartridge receiver 16 for receiving the lens cartridge 14 when assembled, and a movable plunger 18 for forcing a deformable intraocular lens through the lens cartridge 14 into the eye during the implantation operation.

The lens injecting apparatus comprises a tubular body 20 slidably accommodating the movable plunger 18. The tubular body 20 is provided with a cone-shaped portion 22 defining the lens cartridge receiver 16. Specifically, the cone-shaped portion 22 is provided with a cylindrical round hole in the end thereof defining a cylindrical-shaped sleeve for accommodating a portion of the lens cartridge 14. The cone-shaped portion 22 is also provided with a longitudinal slot 24 extending into a transverse slot 26 defining a "bayonet" type connection between the lens cartridge 14 and the lens injecting device 12.

The lens injecting device 12 is also provided with a finger grip 28 allowing a user to grip the lens injecting device 12 between the fore finger and middle finger, and the plunger 18 is provided with a thumb grip 30. The plunger 18 is provided with a spring 31 (FIG. 5) located inside the tubular body 30 and mounted on the plunger 18 of the lens injecting device 12 so that a user pushes the plunger 18 forward against an opposite spring force provided by the spring 31 when gripping the finger grip 28 with the fore finger and middle finger and pressing the thumb grip 30 with the user's thumb.

A first preferred lens cartridge 14 is shown in the closed configuration in FIGS. 2A and 2B and in the open configuration in FIGS. 3A and 3B. A detailed longitudinal cross-sectional view of the lens cartridge 14 is shown in FIG. 6.

The lens cartridge 14 comprises a lens holding portion 32 connected to a nozzle portion 34. Preferably, the lens cartridge 14 is a one-piece construction, for example, made by plastic injection molding with autoclavable plastic (e.g.

polyethylene). However, the lens holding portion 32 and nozzle portion 34 can be made as separate components and assembled together.

The lens cartridge 14 includes an extension 36 set substantially perpendicular relative to a longitudinal axes of the lens cartridge 14 for cooperating with the transverse slot 26 in the cone-shaped portion 22. When loading the lens cartridge 14 into the lens cartridge receiver 16 of the cone-shaped portion 22, the extension 26 is directed into the longitudinal slot 24. The lens cartridge 14 is rotated relative to the lens injecting device 12 so that the extension 26 is then directed into the transverse slot 26 providing a locking "bayonet" type connection between the lens injecting device 12 and lens cartridge 14. This connection arrangement ensures no relative movement between the lens injecting device 12 and the lens cartridge 14 during use of the lens injecting apparatus 10.

The lens cartridge 14 is configured to open and close for loading the deformable intraocular lens into a lens delivery passageway through the lens cartridge 14. In the embodiment shown in FIGS. 1 to 3, the lens holding portion 32 includes a stationary wall portion 38 connected to a movable wall portion 40 by a transverse hinge 42. The hinge 42 is considered "transverse", since the hinge axis is substantially perpendicular or transverse relative to a longitudinal axes of the lens cartridge 14. The longitudinal edges of the movable wall portion 40 may be linear or curvilinear.

The lens cartridge 14 is provided with a lens delivery passageway 44 extending through the lens holding portion 32 into the nozzle portion 34. The back end 46 of the lens cartridge 14 is provided with an opening 48 serving as an entrance (e.g. for plunger tip) into the lens delivery passageway 44, and the front end 50 of the lens cartridge 14 is provided with an opening 52 at nozzle tip 50 serving as an exit (e.g. for deformable intraocular lens) from the lens delivery passageway 44.

The movable wall portion 40 is provided with a protrusion 56 extending inwardly into the lens delivery passageway 44. The protrusion 56 is used to fold a center portion of the deformable intraocular lens into the lens delivery passageway 44 when closing the movable wall portion 40. Specifically, a deformable intraocular lens L (e.g. plate type IOL or three piece type) can be loaded into the lens cartridge 14 by positioning a deformable intraocular lens in a flat configuration so that opposite edge portions of the deformable intraocular lens rest on the open edges 58 of the stationary wall portion 38, as shown in FIG. 3A.

When the movable wall portion 40 is being closed (e.g. by user pressing down on movable wall portion 40 with index finger while supporting stationary wall portion 38 between thumb and fore finger of other hand), the inwardly extending protrusion 56 makes contact with a center portion of the deformable intraocular lens L. As the movable wall portion 40 is further closed, the protrusion 56 forces the center portion of the deformable intraocular lens L downwardly into the lens delivery passageway 44. When the deformable intraocular lens L is fully loaded into the lens delivery passageway, the deformable intraocular lens is folded or bent and in contact with the inner surface of the stationary wall portion 38 (FIG. 4) while opposite edges of the deformable intraocular lens L fold upwardly into opposite grooves 60 provided in the inner surface of the movable wall portion 40.

The hinge 42 is a "live" type hinge molded in the plastic lens cartridge 14 so that the wall thickness decreases to allow bending. Preferably, the wall is thinned from the outside surface of the lens cartridge 14 so that the dimensions of the lens delivery passageway 44 are accurately maintained to prevent any edge that could potentially scrape or otherwise damage the surface of the deformable intraocular lens, in particular the optic portion, when advancing the deformable intraocular lens through the lens delivery passageway 44. Alternatively, the movable wall portion 40 and the remaining portion of the lens cartridge are separate components assembly together along a hinge (e.g. snap-fit interlocking members or hinge pin designs).

In the first embodiment of the lens cartridge 14 shown in FIG. 6, the grooves 60 extend only along the length of the movable wall portion 40. However, the grooves 60 can be extended forward further along lens delivery passageway 44 extending through the lens holding portion 32, or extended even further into the lens delivery passageway of the nozzle portion 34. Further, a single rifled groove (i.e. spiral configuration) can be substituted for the pair of grooves 60 to cause one end of the lens to continue to fold around the remaining portion of the lens to more tightly wrap the deformable intraocular lens as it is advanced through the lens delivery passageway.

The protrusion 56 shown in FIG. 6 tapers downwardly in the direction of the advancing deformable intraocular lens. Alternatively, the protrusion 56 can be modified so as to not taper, or taper in the opposite direction. In addition, the shape of the lower surface of the protrusion 56 can be curvilinear (e.g. concave, convex) continuous, discontinuous, or a combination of shapes, as opposed to being a linear ramp-shaped structure shown in FIG. 6.

The deformable intraocular lens L is loaded into the lens cartridge 14 by positioning the deformable intraocular lens L, as shown in FIG. 3A. Specifically, the deformable intraocular lens L bridges and rests on the edges 58 (FIG. 3B). The user then forces the movable wall portion 40 downwardly while holding the remaining portion of the lens cartridge 14 so that the protrusion 56 forces the center of the deformable intraocular lens L downwardly causing the deformable intraocular lens L to fold along its center into the lens delivery passageway 44. The lens cartridge 14 is then loaded into the lens cartridge receiver 16 of the lens injecting device 12 by aligning the extension 36 of the lens cartridge 14 with the longitudinal slot 24 of the lens injecting device 12. The lens cartridge 12 is force rearwardly, and then rotated to lock the extension 36 into the transverse slot 24.

A second preferred embodiment of the lens cartridge according to the present invention is shown in FIG. 7.

The lens cartridge 14' is provided with a hinge located forward of the extension 36', as opposed to being located behind the extension 36 in the embodiment shown in FIG. 6. This configuration allows a user to grip the extension 36' between the thumb and finger of one hand to facilitate opening the movable wall portion 40'. Optionally, the lens cartridge 14' can also be provided with an additional extension 36' below to facilitate gripping the lens cartridge 14' during opening and closing. Further, the additional extension 36' provides added stability when the lens cartridge 14' is loaded into the lens injecting device 12.

Figure 8:
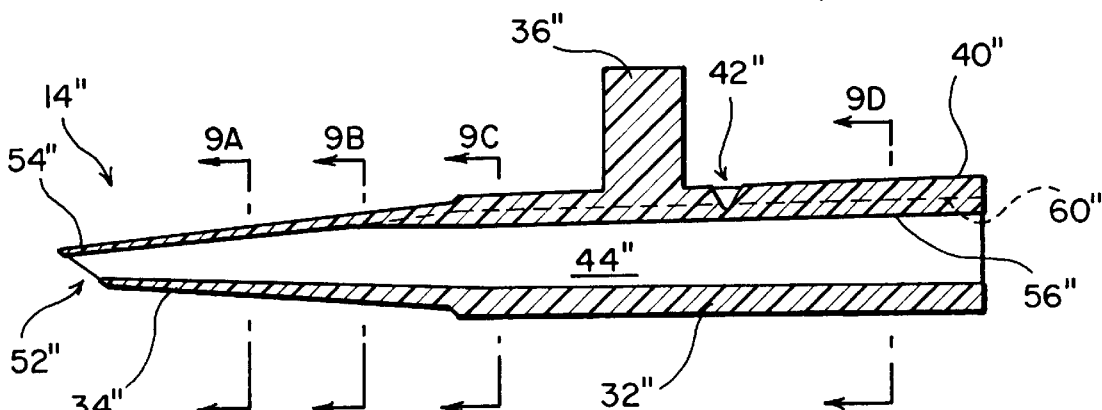
FIG. 8 is a longitudinal cross-sectional view of a third preferred embodiment of the lens cartridge according to the present invention.

A third embodiment of the lens cartridge 14" is shown in FIG. 8.

Figure 9A:
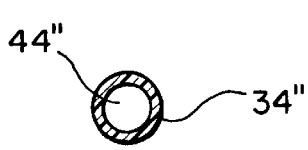
FIG. 9A is a transverse cross-sectional view of the lens cartridge, as indicated in FIG. 8.
Figure 9B:
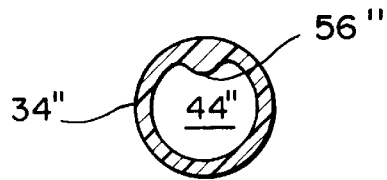
FIG. 9B is a transverse cross-sectional view of the lens cartridge, as indicated in FIG. 8.
Figure 9C:
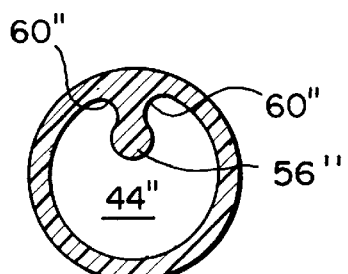
FIG. 9C is a transverse cross-sectional view of the lens cartridge, as indicated in FIG. 8.
Figure 9D:
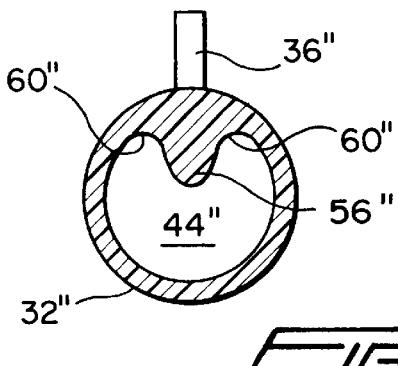
FIG. 9D is a transverse cross-sectional view of the lens cartridge, as indicated in FIG. 8.

The lens cartridge 14" is provided with a pair of grooves 60" (See FIG. 2B) extending along the lens delivery passageway 44" in both the lens holding portion 32" and the nozzle portion 34" (See FIGS. 9A to 9B). The pair of grooves 60" terminate at a position in the nozzle portion 34", however, the pair of grooves 60" can extend further forward and terminate all the way at the nozzle tip 54". Further, the protrusion 56" is shown as having a substantially constant depth along its length except for tapering into the lens delivery passageway 44" in the nozzle portion 34" at the front end of the protrusion 56". Alternatively, the protrusion 56" can taper linearly or curvilinearly in depth in either direction of the lens delivery passageway 44" in other designs.

Figure 10:
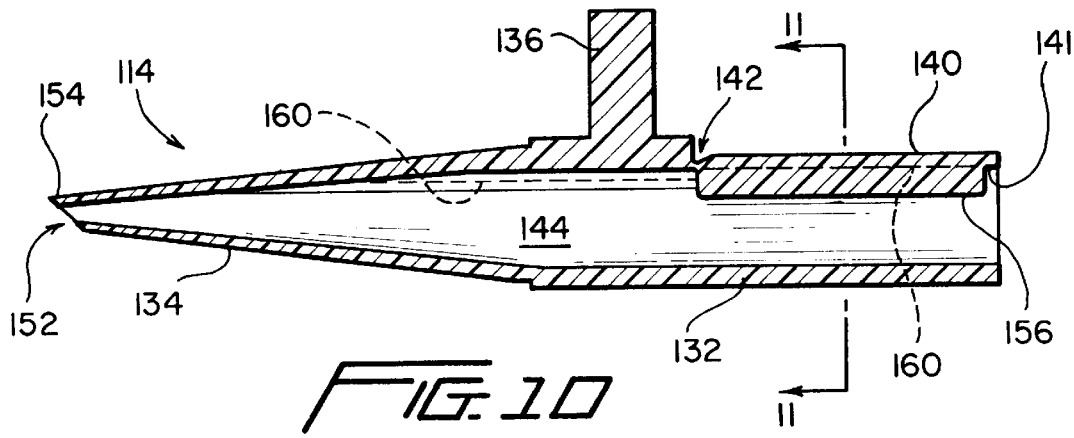
FIG. 10 is a longitudinal cross-sectional view of a fourth preferred embodiment of the lens cartridge according to the present invention.
Figures 11, 13:
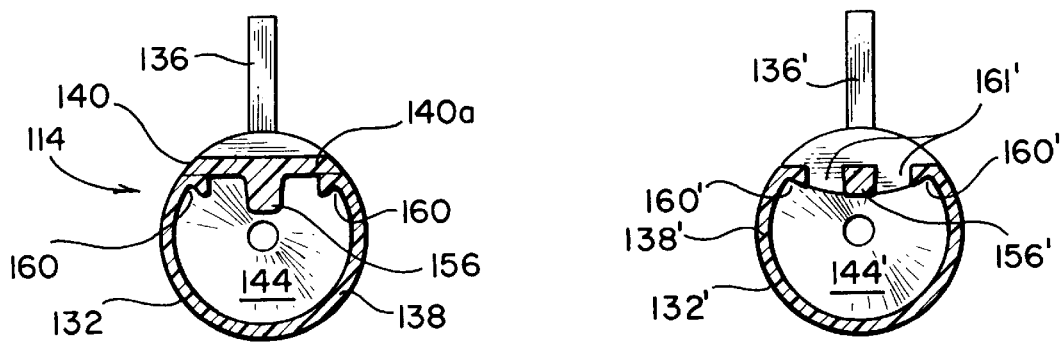
FIG. 11 is a transverse cross-sectional view of the lens cartridge, as indicated in FIG. 10.
FIG. 13 is a transverse cross-sectional view of the lens cartridge, as indicated in FIG. 12.
Figure 12:
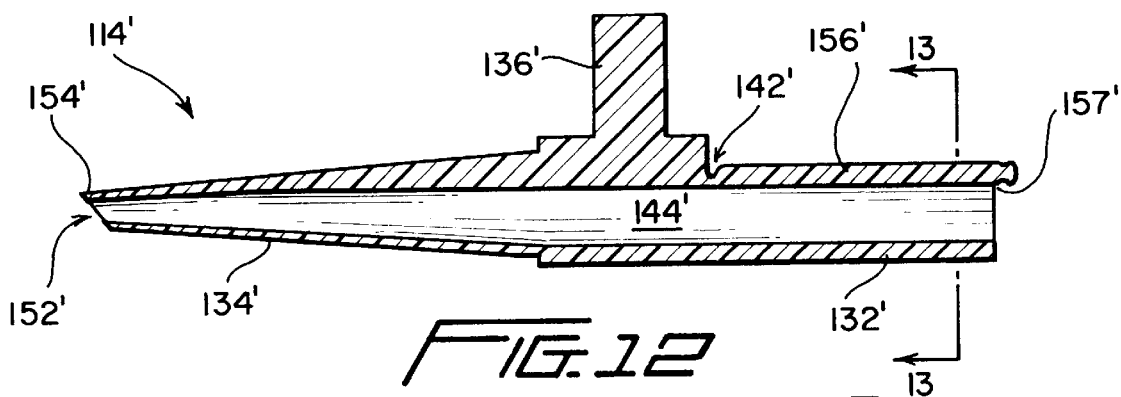
FIG. 12 is a longitudinal cross-sectional view of a fifth preferred embodiment of the lens cartridge according to the present invention.
Figure 14:
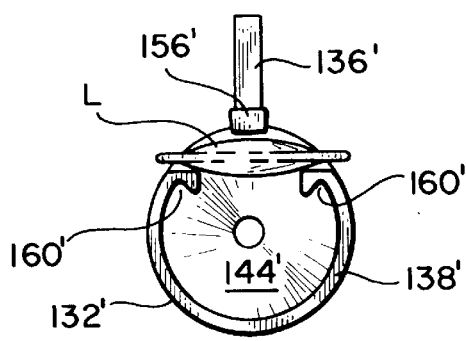
FIG. 14 is a rear end elevational view of the lens cartridge shown in FIG. 12 with a deformable intraocular lens in a flat configuration ready to be loaded into the lens cartridge.
Figure 15:
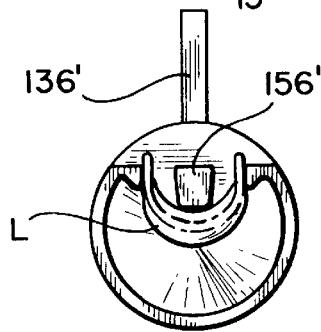
FIG. 15 is a rear end elevational view of the lens cartridge shown in FIG. 12 with a deformable intraocular lens in a partially folded configuration partially loaded into the lens cartridge.

A fourth embodiment of the lens cartridge 114 is shown in FIGS. 10 and 11.

The lens cartridge 114 is provided with a movable wall portion 140 having a flat plate-like arrangement with a protrusion 156 extending inwardly into the lens delivery passageway 144. The flat plate-like arrangement allows for a wider hinge connection improving strength and opening stability verses the more point-like hinge connection of the embodiment shown in FIG. 3B. Further, the pair of grooves 160 are provided in the stationary wall portion 138 as opposed to the movable wall portion 40 in the embodiment shown in FIG. 3B. In addition, the movable wall portion 140 is provided with an indent 141 at its free end to provide a catch to facilitate opening the lens cartridge 114.

A fifth preferred embodiment of the lens cartridge 114' is shown in FIGS. 12 to 15.

The lens cartridge 114' is provided with a movable wall portion defined by a hinged cantilever member 156' for inserting the deformable intraocular lens into the lens delivery passageway 144'. In this embodiment, even with the cantilever member 156' closed, the lens delivery passageway 144' through the lens holding portion 132' remains partially open due to the pair of slots 161' located on either sides of the cantilever member 156' (See FIG. 13). The cantilever member 156' is provided with an extended tip 157' to facilitate lifting the cantilever member 156' for loading the deformable intraocular lens. In an alternative embodiment, the cantilever member 156' is not hinged, thus, relying on its resilience to bend along its length to provide a hinge-like action for loading the deformable intraocular lens.

Figure 16:
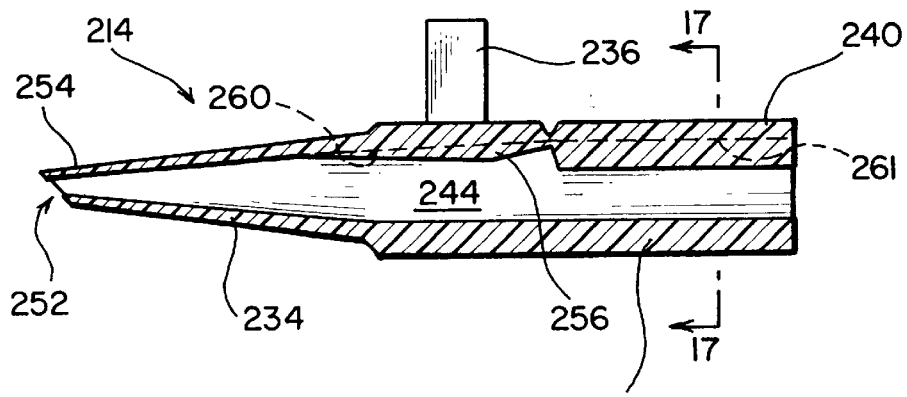
FIG. 16 is a side longitudinal cross-sectional view of a sixth preferred lens cartridge according to the present invention.
Figure 17:
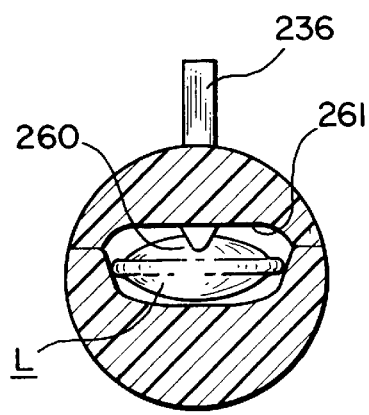
FIG. 17 is a transverse cross-sectional view of the lens cartridge, as indicated in FIG. 16.

A sixth preferred embodiment of the lens cartridge according to the present invention is shown in FIGS. 16 and 17.

The lens cartridge 214 is configured for loading a deformable intraocular lens L in a flat configuration, as shown in FIG. 17. This is accomplished by providing an oval-shaped lens delivery passageway in the lens holding portion 232. The movable wall portion 240 is provided with a non-contoured essentially flat inner top wall 261 (i.e. no pair of grooves). Alternatively, the inner wall of the movable wall portion 261 can be provided with some surface contouring to begin folding the flat loaded lens when closing the movable wall portion 261.

In this embodiment the forward end of the lens holding portion 232 and part of the nozzle portion 234 are provided with a ramp-shaped protrusion 256 dividing a pair of grooves in front of the movable wall portion 240 to facilitate folding of the deformable intraocular lens as it is advanced forward.

Figure 18:
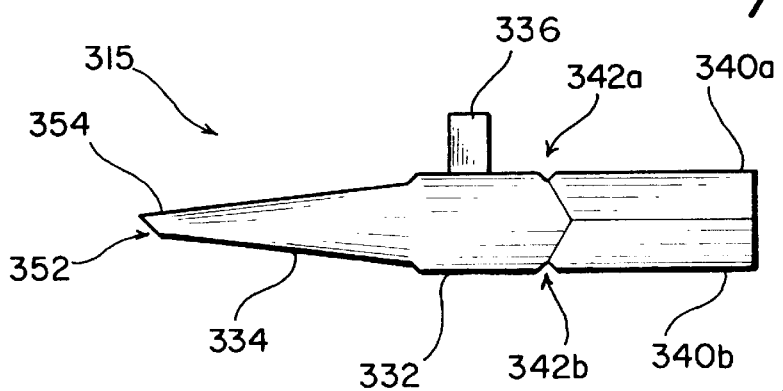
FIG. 18 is a side elevational view of a seventh preferred embodiment of the lens cartridge according to the present invention in a closed configuration.
Figure 19:
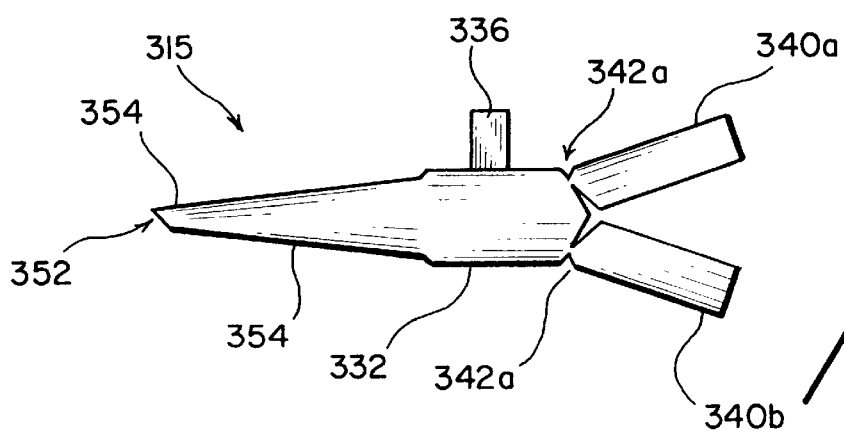
FIG. 19 is a side elevational view of the seventh preferred embodiment of the lens cartridge according to the present invention in an open configuration.

A seventh embodiment of the lens cartridge according to the present invention is shown in FIGS. 18 and 19.

The lens cartridge 315 is provided with an upper movable wall portion 340*a* and a lower movable wall portion 340*b*. The upper movable wall portion 340*a* is connected to a remaining portion of the lens holding portion 332 by hinge 342*a*, and the lower movable wall portion 340*b* is connected to the remaining portion of the lens holding portion by hinge 342*b*. Thus, this is a double-hinge type design with no stationary wall portion characteristic of the embodiment shown in FIGS. 2 and 3.

What is claimed is:

1. A deformable intraocular lens injecting apparatus, comprising:

a lens cartridge including a lens holding portion connected to a nozzle portion, said lens cartridge having a lens delivery passageway extending through said lens holding portion into said nozzle portion, said lens holding portion including a stationary wall portion and a single movable wall portion, said stationary wall portion immovable relative to said nozzle portion, said movable wall portion connected to said stationary wall portion by a transverse hinge oriented substantially perpendicular relative to said lens delivery passageway to allow the lens holding potion to be opened to load the deformable intraocular lens into the stationary wall portion and then closed to enclose the deformable intraocular lens inside the lens delivery passageway.

2. An apparatus according to claim 1, wherein said transverse hinge is a live hinge.

3. An apparatus according to claim 1, wherein said lens holding portion is tubular.

4. An apparatus according to claim 3, wherein said stationary wall portion is located along a bottom portion of said lens cartridge and said movable wall portion is located along a top portion of said lens cartridge allowing the deformable intraocular lens to be cradled by said stationary wall portion when loaded in said lens holding portion and then covered by said movable wall portion.

5. An apparatus according to claim 4, wherein said movable wall portion is a smaller circumferential segment and said stationary wall portion is a larger circumferential segment of said tubular lens holding portion.

6. An apparatus according to claim 3, wherein said movable wall portion is a smaller circumferential segment and said stationary wall portion is a larger circumferential segment of said tubular lens holding portion.

7. An apparatus according to claim 3, wherein said movable wall portion includes a movable end and a hinged end.

8. An apparatus according to claim 7, wherein said movable end of said movable wall portion is positioned at a back end of said lens cartridge and said transverse hinge is located forward of said back end of said lens cartridge to allow the lens holding portion to be opened from said back end of said lens cartridge.

9. An apparatus according to claim 8, wherein a width of said movable wall portion tapers downwardly in a direction from a free end of said movable wall portion towards said transverse hinge.

10. An apparatus according to claim 9, wherein longitudinal edges of said movable wall portion are linear.

11. An apparatus according to claim 9, wherein longitudinal edges of said movable wall portion are curvilinear.

12. An apparatus according to claim 11, wherein said curvilinear edges are arc-shaped segments extending outwardly along the lengths of said curvilinear edges.

13. An apparatus according to claim 1, wherein said movable wall portion includes a movable end and a hinged end.

14. An apparatus according to claim 13, wherein said movable end of said movable wall portion is positioned at a back end of said lens cartridge and said transverse hinge is located forward of said back end of said lens cartridge to allow the lens holding portion to be opened from said back end of said lens cartridge.

15. An apparatus according to claim 1, wherein a width of said movable wall portion tapers downwardly in a direction from a free end of said movable wall portion towards said transverse hinge.

16. An apparatus according to claim 1, wherein said movable wall portion releasably locks with said stationary wall portion when closed.

17. An apparatus according to claim 1, wherein said movable wall portion substantially permanently locks with said stationary wall portion when closed.

18. An apparatus according to claim 1, wherein said lens delivery passageway is contoured for folding or further folding the deformable intraocular lens when the deformable intraocular lens is being advanced through the lens delivery passageway.

19. An apparatus according to claim 18, wherein said lens delivery passageway includes at least one groove.

20. An apparatus according to claim 19, wherein said lens delivery passageway includes a pair of grooves separated by an inwardly extending protrusion.

21. An apparatus according to claim 20, wherein said grooves taper inwardly inside the lens delivery passageway in a direction of advancing the deformable intraocular lens.

22. An apparatus according to claim 21, wherein said grooves exist in only a portion of the lens delivery passageway extending through said lens holding portion of said lens cartridge.

23. An apparatus according to claim 21, wherein said grooves exist in the lens delivery passageway through said lens holding portion and extend into said nozzle portion of said lens cartridge.

24. An apparatus according to claim 20, wherein said pair of grooves are located in the inner surface of the movable wall portion.

25. An apparatus according to claim 20, wherein said pair of grooves are located in the inner surface of the stationary wall portion.

26. An apparatus according to claim 19, wherein transverse cross-sections of said lens delivery passageway taper inwardly in a direction of advancing the deformable intraocular lens.

27. An apparatus according to claim 18, wherein transverse cross-sections of said lens delivery passageway taper inwardly in a direction of advancing the deformable intraocular lens.

28. An apparatus according to claim 1, wherein transverse cross-sections of said lens delivery passageway taper inwardly in a direction of advancing the deformable intraocular lens.

29. An apparatus according to claim 1, further including a lens injecting device including a lens cartridge receiver and a movable plunger, said lens cartridge receiver configured for receiving said lens cartridge.

30. An apparatus according to claim 1, wherein said movable wall portion is configured for at least partially folding the deformable intraocular lens when closing.

31. An apparatus according to claim 30, wherein said movable wall portion includes a protrusion extending inwardly into said lens delivery passageway.

32. An apparatus according to claim 31, wherein said movable wall portion is configured for forcing a center portion of the deformable intraocular lens inwardly into said lens delivery passageway to fold the lens into the lens delivery passageway.

33. An apparatus according to claim 32, wherein said lens cartridge is configured so that opposite edges of the deformable intraocular lens are supported by edges of the stationary wall portion while said inwardly extending protrusion of the movable wall portion acts on the center of the deformable intraocular lens when closing the movable wall portion for effectively folding the deformable intraocular lens into the lens delivery passageway.

* * * * *